United States Patent [19]

Koch et al.

[11] 4,042,595
[45] Aug. 16, 1977

[54] PROCESSES FOR THE PRODUCTION OF HETEROCYCLIC COMPOUNDS

[75] Inventors: Paolo Koch, San Giuliano Milanese; Emilio Perrotti, San Donato Milanese, both of Italy

[73] Assignee: Snam Progetti S.p.A., San Donato Milanese, Italy

[21] Appl. No.: 655,052

[22] Filed: Feb. 4, 1976

Related U.S. Application Data

[63] Continuation of Ser. No. 491,863, July 25, 1974, abandoned.

[30] Foreign Application Priority Data

Aug. 1, 1973    Italy .................................. 27389/73

[51] Int. Cl.$^2$ .................... C07D 339/06; C07D 263/22
[52] U.S. Cl. ................................. 260/307 C; 544/54; 544/96; 544/97; 260/306.7 R; 260/327 M
[58] Field of Search ....... 260/327 M, 307 C, 306.7 R, 260/243 R, 244 R

[56] References Cited

U.S. PATENT DOCUMENTS

2,868,801    1/1959    Steele ............................. 260/307 C

OTHER PUBLICATIONS

Mahan, College Chemistry, Addison Wesley, Reading, Mass., 1966, p. 500.

Primary Examiner—R. Gallagher
Attorney, Agent, or Firm—James V. Costigan

[57] ABSTRACT

A ketonic heterocyclic compound having at least two heteroatoms in the ring is prepared by reacting a difunctional compound having the general formula

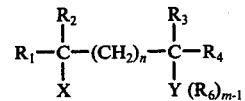

in which $R_1$, $R_2$, $R_3$ and $R_4$ are members of the group consisting of aliphatic, aromatic, cycloaliphatic and heterocyclic hydrocarbons which may contain functional groups selected from —OH, —OR$_5$, —COOH, —COOR$_5$, —CN, —Cl, —Br, —I, —F, and —CO—R$_5$, wherein R$_5$ is an aliphatic, aromatic, cycloaliphatic or heterocyclic hydrocarbon; X is oxygen or sulphur; Y is sulphur or nitrogen; $n$ is an integer ranging from 1 to 3, or zero; R$_6$ is a hydrogen or a hydrocarbon radical included in the above definition of $R_1 R_2 R_3$ and $R_4$; and $m$ is the valence of Y, with carbon monoxide and oxygen in the presence of a catalyst selected from selenium, selenium compounds and complexes of copper, in the temperature range of from room temperature to 80° C and in the pressure range of from 1 to 10 atmospheres.

3 Claims, No Drawings

PROCESSES FOR THE PRODUCTION OF HETEROCYCLIC COMPOUNDS

This is a continuation, of application Ser. No. 491,863 filed July 25, 1974, now abandoned.

The present invention relates to a process for the production of heterocyclic compounds.

More particularly the present invention relates to a process for the production of ketonic heterocyclic compounds having at least two heteroatoms in the ring.

The products obtained by means of the inventive process have the following general formula

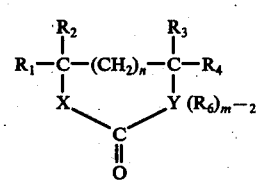
(1)

in which $R_1$, $R_2$, $R_3$, $R_4$ are aliphatic, cycloaliphatic or heterocyclic hydrocarbons which may contain also functional groups such as —OH, —$OR_5$, —COOH, $COOR_5$, —CN, —Cl, —Br, —I, —F, —CO-$R_5$ wherein $R_5$ is an aliphatic, aromatic, cycloaliphatic or heterocyclic hydrocarbon; X is oxygen or sulphur; Y is sulphur or nitrogen; n is an integer ranging from 1 to 3, or may be zero; ($R_6$) may be hydrogen or a hydrocarbon radical having the same meaning as $R_1$, $R_2$, $R_3$ and $R_4$ and m is the valence of Y.

The aforesaid products are useful in many fields (see, Chemical Review, 1967, pp. 233-236). They have been prepared in the past through a reaction between a difunctional compound and phosgene or by means of more complex syntheses.

The use of phosgene involves several drawbacks because its toxicity and of its reactivity with other functional groups also present in the molecule.

We have now found a simple and cheap process which makes it possible to obtain the aforesaid compounds at very high yields.

The inventive process consists in reacting a difunctional compound having the general formula.

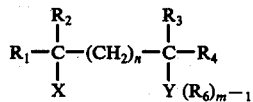
(2)

in which $R_1$, $R_2$, $R_3$, $R_4$, $R_6$ and X, Y, n and m have the aforesaid meanings, with carbon monoxide and oxygen in the presence of a suitable catalyst.

The reaction may be carried out either in the homogeneous phase by dissolving the reagents and the catalyst in a suitable solvent or in the heterogeneous phase by using an insoluble catalyst.

Unrestrictive examples of compounds according to the formula (2) may be ethanolamine, 2-aminopropanol, 3-aminopropanol, diethanolamine, 1,2-ethanedithiol, 1,3-propanedithiol, 1,2-propandithiol, 2-aminoethanethiol, 2-aminopropanthiol, 3-aminopropanthiol.

The reaction may be carried out under a pressure ranging from 1 to 100 atmospheres. Preferably use is made of the range from 1 to 10 atmospheres for practical reasons.

As noted above, the catalyst may be soluble in the reagents or in suitable solvents, or it may be insoluble.

Among the soluble catalysts it is possible to mention metallic selenium and the derivatives thereof whereas, as to the insoluble catalysts, an advantageous use may be made of complexes containing Cu. The reaction may be carried out at temperatures ranging from 0° to 100° C, preferably from the room temperature to 80° C.

The following examples illustrate the invention, but are not limitative thereof.

EXAMPLE 1

23.8 mmoles of 1-2 dimercaptoethane, 1 mmole of triethylamine and 0.5 mmole of Se were reacted in 10 ml of THF at 25° C with a $CO:O_2$ mixture in the molar ratio 10:1 at 3.5 atmospheres.

After 40 hours selenium was recovered and the solvent was evaporated from the resulting suspension. The residue was distilled under vacuum. Through mass analyses the distilled product was shown to be ethylenedithiocarbonate. Yield = 90%.

EXAMPLE 2

10 mmoles of 2-3 dimercapthopropanol-1, 1 mmole of triethylamine and 1 mmole of Se were reacted in 10 ml of THF at 25° C with a CO—$O_2$ mixture in the molar ratio of 10:1 at 3:5 atmospheres.

After 16 hours Selenium was recovered from the resulting suspension and the solvent was evaporated. The residue was distilled under vacuum. The distilled product, through IR and mass analysis, was shown to be 1-3 dithiolan-2-one-4-hydroxmethyl. Yield = 90%.

20 mmoles of 2-3 dimercaptoapropanol, 1 mmole of thioethylamine and 0.5 mmole of Se were reacted with CO and $O_2$ under conditions similar to the preceding ones. After 16 hours the solution was weakly yellow coloured and homogeneous. The solvent was evaporated and the residue was distilled.

18 mmoles of 1-3 dithiolan-2-one-4-hydroximethyl were obtained. Yield = 90%.

EXAMPLE 3

14.8 mmoles of 2-mercaptoethylamine and 0.5 mmole of amorphous Se, in 10 ml of THF, were reacted at 60° C with a $CO:O_2$ mixture in the molar ratio 10:1 at 3.5 atmospheres.

After 4 hours the solution was filtered from selenium and the solvent was evaporated. The residue was again crystallized in $CS_2$ (m.p. = 50° C). 1.4 g of 2-thiazolidinone were obtained, identified through IR and mass spectoscopy. Yield = 93%.

EXAMPLE 4

5.14 mmoles of cysteinethylester and 0.3 mmole of amorphous Se in 80 ml of THF were reacted at 60° C under conditions similar to the preceding ones.

After the evaporation of the solvent, 0.85 g of an oily product was isolated. Through IR and mass analysis it proved to be 2-thiazolidinone-4-carbethoxy. Yield = 94%.

EXAMPLE 5

82 mmoles of ethanolamine and 1 mmole of amorphous selenium were reacted in 25 ml of THF with a $CO:O_2$ mixture in the molar ratio 4:1 at 4 atmospheres. After 3 hours at 70° C selenium was filtered and the solvent was evaporated. The residue was crystallized from chloroform (m.p. = 87° C).

6.8 g of product was obtained. Through IR analysis it was shown to be 2-oxazolidone. Yield = 95%.

EXAMPLE 6

12.7 mmoles of 1-amino-2-propanol and 0.3 mmole of selenium were reacted at 60° C under conditions similar to the preceding ones. After 3 hours selenium was filtered, the solvent was evaporated and the residual product was distilled under vacuum.

1.2 g of an oily product were obtained. Through IR and mass analysis it was shown to be 2-oxazolidone-5-methyl. Yield = 95%.

EXAMPLE 7

10 mmoles of diethanoleamine and 0.3 mmole of selenium were reacted at 60° C under under conditions similar to the preceding ones.

After 10 hours selenium was filtered, the solvent was evaporated and the residue was distilled under vacuum. 1.2 g of liquid product were obtained. Through IR and mass analysis it was shown to be 2-oxazolidone-3-hydroxyethyl. Yield = 91%.

EXAMPLE 8

10.3 mmoles of trihydroxymethylaminomethane and 0.5 mmole of selenium were reacted in 20 ml of ethyl alcohol at 70° C with a $CO:O_2$ mixture in the molar ratio 4:1 at 4 atmospheres. After 5 hours selenium was filtered and the solvent was evaporated. The residue was crystallized from chloroform (m.p. = 104° C). 1.5 g of product were obtained. Through IR analysis it was shown to be 2-oxazolidone-4,4-bis-hydroxymethyl. Yield = 99%.

EXAMPLE 9

16.6 mmoles of ethanolamine and 10 mmoles of CuCl in 10 ml of pyridine were treated, in an autoclave at 70° C, with a $CO:O_2$ mixture in the molar ratio 4:1. After 16 hours the solution was filtered and the solvent evaporated under vacuum. The residue was crystallized from chloroform. 0.78 g of 2-oxazolidone was obtained. Yield = 55%.

What we claim is:

1. A process for the preparation of ethylenedithiocarbonate which comprises reacting 1,2-dimercaptoethane with carbon monoxide and oxygen in the presence of a selenium catalyst.

2. A process for the preparation of 1,3-dithiolan-2-one-4-hydroxymethyl which comprises reacting 2,3-dimercaptopropanol-1 with carbon monoxide and oxygen in the presence of a selenium catalyst.

3. A process for the preparation of 2-oxazolidone which comprises reacting ethanolamine with carbon monoxide and oxygen in the presence of a cuprous chloride catalyst.

* * * * *